(12) United States Patent
Bedingham et al.

(10) Patent No.: US 6,756,225 B2
(45) Date of Patent: Jun. 29, 2004

(54) AUTOMATED IMAGING AND HARVESTING OF COLONIES ON THIN FILM CULTURE DEVICES

(75) Inventors: William Bedingham, Woodbury, MN (US); Raj Rajagopal, Woodbury, MN (US); Michael G. Williams, Vadnais Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 449 days.

(21) Appl. No.: 09/797,343

(22) Filed: Mar. 1, 2001

(65) Prior Publication Data

US 2002/0110906 A1 Aug. 15, 2002

Related U.S. Application Data

(63) Continuation-in-part of application No. 09/733,223, filed on Dec. 8, 2000.

(51) Int. Cl.[7] .............................................. C12M 1/22
(52) U.S. Cl. ................................ 435/305.1; 435/288.3; 435/305.4
(58) Field of Search ........................... 435/288.3, 288.4, 435/288.7, 305.1, 305.2, 305.3, 305.4

(56) References Cited

U.S. PATENT DOCUMENTS

| | | | |
|---|---|---|---|
| 4,565,783 A | 1/1986 | Hansen et al. | 435/299 |
| 5,089,413 A | 2/1992 | Nelson et al. | 435/254 |
| 5,232,838 A | 8/1993 | Nelson et al. | 435/30 |
| 5,364,766 A | 11/1994 | Mach et al. | 435/34 |
| 5,393,662 A | 2/1995 | Roth et al. | 435/38 |
| 5,403,722 A | 4/1995 | Floeder et al. | 435/39 |
| 5,462,860 A | 10/1995 | Mach | 435/34 |
| 5,510,246 A | 4/1996 | Morgan | 435/39 |
| 5,573,950 A | 11/1996 | Graessle et al. | 435/287.3 |
| 5,601,998 A | 2/1997 | Mach et al. | 435/34 |
| 5,681,712 A | 10/1997 | Nelson | 435/30 |
| 5,694,478 A | 12/1997 | Braier et al. | 382/133 |
| 5,723,308 A | 3/1998 | Mach et al. | 435/34 |
| 5,744,322 A | 4/1998 | Krejcarek et al. | 435/39 |
| 5,747,333 A * | 5/1998 | Jungmann-Campello et al. | 435/283.1 |
| 5,928,858 A * | 7/1999 | Chao | 435/4 |

FOREIGN PATENT DOCUMENTS

| | | | |
|---|---|---|---|
| GB | 2 310 006 | 8/1997 | F15B/15/14 |
| WO | WO 00/25923 | 5/2000 | B01L/3/02 |

OTHER PUBLICATIONS

Brochure "CLONTECH CLONdisc™ Plates—The New Paradigm in Plating", (2000).
Williams et al., U.S. patent application Ser. No. 09/541,416, "Device for Propagation and Storage of Microorganisms", filed Apr. 3, 2000.

* cited by examiner

*Primary Examiner*—David A. Redding
(74) *Attorney, Agent, or Firm*—Nancy M. Lambert

(57) ABSTRACT

Thin film culture devices are described that have positioning structures, as well as methods for harvesting cells from colonies on the culture device based on location of colonies on the device relative to the positioning structures. In addition, a computer readable medium encoded with a computer program is described that identifies position of colonies relative to the positioning structures.

12 Claims, 9 Drawing Sheets

(1 of 9 Drawing Sheet(s) Filed in Color)

AUTOMATED IMAGING AND HARVESTING OF COLONIES ON THIN FILM CULTURE DEVICES

This application is a continuation-in-part of application Ser. No. 09/733,223, filed Dec. 8, 2000.

BACKGROUND

This invention relates to a method for imaging and harvesting cells from a microbial colony on a thin film culture device.

Many recombinant and molecular cloning techniques rely on the ability to culture bacteria on an agar plate and to select particular colonies from the agar for further study. Each colony is typically selected manually with a sterile toothpick, which can be quite laborious. In addition, there can be uncertainty when a researcher attempts to relocate the same colony from the original agar plate.

Accordingly, automated systems have been used to identify and mark a colony growing on a culture device. For example, automated colony picking systems, such as a BIO-PICK automated colony picking system sold by Biorobotics, Inc., Cambridge, U.K., have been developed to increase the speed with which recombinant E. coli colonies can be processed for genetic research. Typically, these systems include an imaging component, such as a CCD camera, and a robotic arm that positions a "pin" over each colony and mechanically "picks" a portion of the colony material from agar culture plates. The colony material from the agar plates is then transferred to culture medium or reagents for growth of the cells or for amplification or analysis of the genetic material within the transferred material.

SUMMARY

The invention features thin film culture devices with positioning structures and methods for harvesting cells from colonies present on such culture devices. Images of the culture devices are obtained and positions of colonies growing or present on such culture devices are identified relative to the positioning structures to allow cells to be harvested from colonies based on the identified positions of the colonies. The positioning structures are useful for realigning the culture device such that cells from colonies on the culture device can be harvested at any time.

In one embodiment, the invention is a culture device for the propagation or storage of microorganisms. The device includes a self-supporting, waterproof substrate and a cover sheet (e.g., a transparent cover sheet), wherein a gelling agent is contained on the self-supporting substrate, and wherein the self-supporting substrate and the cover sheet include positioning structures, e.g., holes, slits, slots, beveled edges, notches, or raised structures. The culture device may further include a barcode label on a surface of the culture device. The self-supporting substrate may further include a spacer and/or a growth medium (e.g., containing one or more nutrients). The culture device may further include an indicator and a corresponding inducer. The cover sheet may further include a gelling agent and/or a reinforcement layer, such as a foam, a film, or a non-woven material.

In another embodiment, the invention is a culture device for the propagation or storage of microorganisms that includes first and second layers that are separable from each other. The first and second layers may include a gelling agent such as guar gum, xanthan gum, locus bean gum, polyvinyl alcohol, carboxymethylcellulose, alginate, polyvinylpyrrolidone, gellan, or low monomer content polyacrylic acid. The first and second layers also include positioning structures such as holes, beveled edges, slits, slots, notches, or raised structures. The first or second layers may include a spacer. The first layer may further include a growth medium. The growth medium may include a detergent or a salt. The first layer may also include a selectable agent. The first or second layer may further include a reinforcement layer.

In another embodiment, the invention is a system for harvesting cells from a colony on a thin film culture device having positioning structures. The system includes a scanner, a processing unit and a picking apparatus. The scanner obtains and provides an image file to the processing unit. The processing unit identifies and selects, if necessary, cell colonies on the culture device and provides the position of the colonies relative to the positioning structures to the picking apparatus. The picking apparatus harvests the cells from the colonies based on the position. The picking apparatus may have an orienting unit, wherein the orienting unit has receiving structures adapted to receive corresponding positioning structures in the culture device. The orienting unit may further include a compliant pad. The picking apparatus can include a liquid handling tip.

In yet another embodiment, the invention is a picking apparatus for harvesting cells from a colony on a thin film culture device having positioning structures. The picking apparatus includes an orienting unit, wherein the orienting unit positions the colony relative to the positioning structures; and a picking arm, wherein the picking arm is programmed with the position of a selected colony relative to the positioning structures and is adapted to contact cells of the selected colony based on the position. The orienting unit has receiving structures adapted to receive corresponding positioning structures in the culture device.

A method for harvesting cells from colonies on a culture device also is another embodiment of the invention. The method includes the steps of providing a thin film culture device having positioning structures; obtaining an image of the culture device including cell colonies on the surface of the device (e.g., by scanning the culture device); processing the image to provide positions of cell colonies relative to the positioning structures of the device; optionally selecting particular cell colonies; and then contacting the cell colonies with a picking apparatus based on the position and/or selection of cell colonies to harvest the cells. The picking apparatus may be moved in at least one or at least two directions from the contact point to harvest the cells. Processing the image may include identifying a location of the positioning structures; identifying a location of one or more colonies, optionally selecting a specific colony; and calculating a position of the selected colony relative to the positioning structures. The position of the colonies relative to the positioning structure may include X-Y coordinates.

In another embodiment, the invention is a computer readable medium having instructions thereon causing a programmable processor to display an image of a thin film culture device having positioning structures on a display device; differentiate positioning structures from colonies on the culture device; identify locations of the positioning structures; identify locations of the colonies and/or selected colonies; and calculate positions of the colonies relative to the positioning structures. The computer readable medium may be a storage medium for storing instructions or may be a transmission medium for transmitting the instructions.

The invention includes a computer readable medium having an image stored therein, wherein the image contains image data representative of colonies on a thin film culture device having positioning structures and a computer readable medium having data stored therein, wherein the data are the coordinates of colonies on a culture device relative to positioning structures on the culture device.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
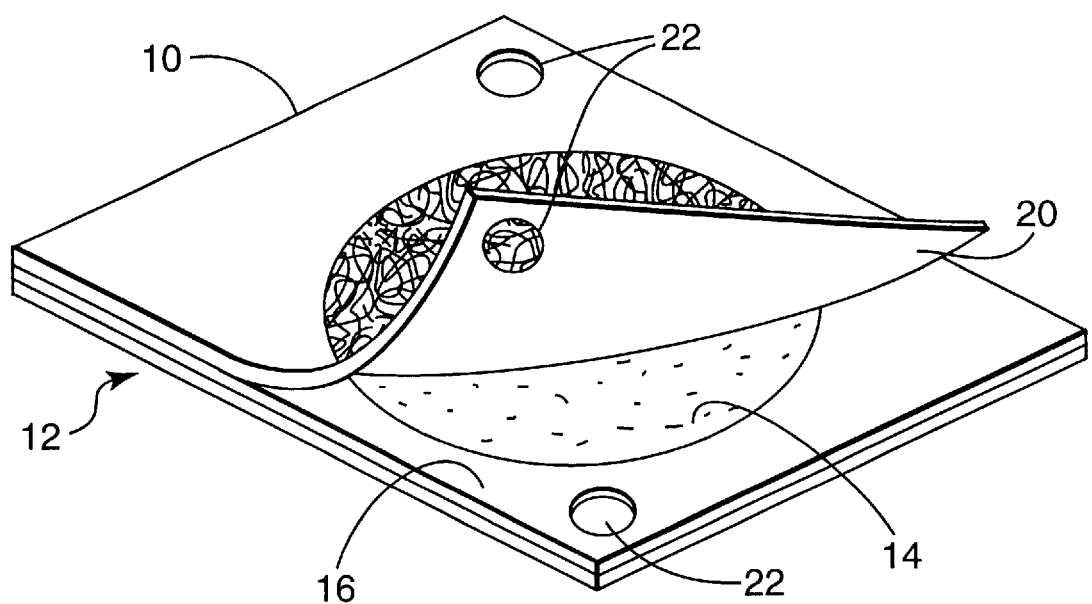
FIG. 1 is a schematic of a thin film culture device having positioning structures.

Thin film culture devices of the invention are useful for molecular cloning techniques, and provide many advantages over traditional culture devices, such as petri dishes, which typically contain semisolid nutrient agar medium, and multi-well devices containing nutrient broth medium. One advantage of the thin film culture devices of the invention is that they are "sample-ready" and require no preparation before use. Thin film culture devices of the invention also are more compact than traditional petri dishes, making them highly suitable for imaging microbial colonies contained on these devices with an inexpensive, flatbed scanning device.

Incorporation of positioning structures, such as holes, slots, and notches, on the thin film devices of the invention allows the devices to be oriented such that the precise position of the microbial colonies within the culture device can be mapped and, subsequently, allows cells from the mapped colonies to be picked using an automated picking apparatus. In addition, colonies, either similar or different from one another, from multiple thin film culture devices can be mapped simultaneously. The positioning structures provide a reference position such that at a future time, the culture devices can be realigned and cells from the colonies may be harvested based on the original map.

Culture Devices

Suitable thin film culture devices can be constructed generally as described in U.S. Pat. Nos. 4,565,783; 5,089,413; 5,232,838; and 5,601,998. For example, culture device 10, which includes a body member having a self-supporting, waterproof substrate 12 may be used (see FIG. 1). Substrate 12 is preferably a relatively stiff material made of a waterproof or water impermeable material (i.e., does not absorb water) such as polyester, polypropylene, or polystyrene. Other suitable waterproof materials include substrates such as paper containing a waterproof polyethylene coating.

The upper surface of substrate 12 may contain a layer of culture medium 14, which is dried to provide a dry medium on substrate 12. Alternatively, a layer of adhesive may be coated on substrate 12, which serves to hold a culture medium that may be applied as a powder. The adhesive should be sufficiently transparent when hydrated to allow viewing of microbial colonies, e.g., bacterial colonies, growing on the surface of the substrate through the coated substrate. The adhesive should also be coated on the substrate in a thickness that allows the substrate to be uniformly coated with dry culture medium without completely embedding the medium in the adhesive.

If the culture medium is to be used in a dry form or as a dry powder, the components, e.g., nutrients, gelling agents, and indicator may be added as a liquid to the substrate and then dried. The culture medium may be readily dried by heating liquid medium in an oven at about 104° C. until essentially all of the water in the liquid has evaporated. If the medium is heated after the water has evaporated, however, the medium begins to degrade.

A spacer 16 having a circular opening in the center may be adhered to the medium coated surface of substrate 12. The portion of spacer 16 that covers the periphery of substrate 12 defines the area that is to be inoculated with a sample and serves to prevent the sample from leaking from the substrate. Spacer 16 may be any non-absorbent material such as plastic, including foamed plastic (i.e., a foam) or a non-absorbent non-woven material. Alternatively, a device may not include spacer 16. In this device, the amount of sample is contained on the substrate by the components of the medium alone.

Cover sheet 20 may be attached to one edge of an upper surface of spacer 16. Cover sheet 20 is preferably made of a transparent film or sheet material in order to facilitate visualizing of microbial colonies present on the substrate. In addition, cover sheet 20 is preferably impermeable to bacteria and water vapor in order to avoid the risk of contamination and deterioration of the components A preferred material for use as a cover sheet 20 is biaxially oriented polypropylene. The cover sheet is typically coated with a gelling agent such as a gum and, in some embodiments, a second indicator. Cover sheet 20 may include a reinforcement layer, such as a non-woven material, foam (e.g., a polystyrene foam), or film (e.g., a polycarbonate film), for additional support.

Self-supporting substrate 12 and cover sheet 20 each contain positioning structures 22, which allow the culture device to be oriented. Positioning structures 22 may be holes (as pictured in FIG. 1), slits, slots, beveled edges, protrusions or other raised structures, notches, or any other structure that may be used to orient the culture device. Typically, two or more positioning structures are contained on the thin film culture device. It should be noted, however, that a thin film culture device may contain a single positioning structure if, during the harvesting step, the single positioning structure may be used in combination with the overall configuration of the thin film culture device to be oriented. In addition, combinations of positioning structures may be used, e.g., a hole and a notch. A barcode label may also be on a surface of the culture device to aid sample tracking and identification of the culture device.

In use, a predetermined amount of inoculum, typically about 1 to 5 ml (e.g., 2–3 ml) of inoculum, is added to the device illustrated in FIG. 1 by pulling back cover sheet 20 and adding the inoculum (e.g., an aqueous microbial suspension) to the middle of culture medium 14. Cover sheet 20 is then replaced over substrate 12 and the inoculum is evenly spread on the substrate. A convenient tool to do this is a weighted circular template, which also is used to confine the inoculum to a specific area of substrate 12. As the inoculum contacts and is spread on substrate 12, the culture medium on substrate 12 hydrates to form a growth-supporting nutrient gel. The inoculated device is then incubated for a predetermined time after which the number of microbial colonies growing on the substrate may be visualized, and, optionally, counted through the transparent cover sheet 20. Alternatively, a gelling agent is contained on substrate 12 in place of culture medium 14. In such an embodiment, culture medium is added before inoculation or during the inoculation step.

Figure 2:
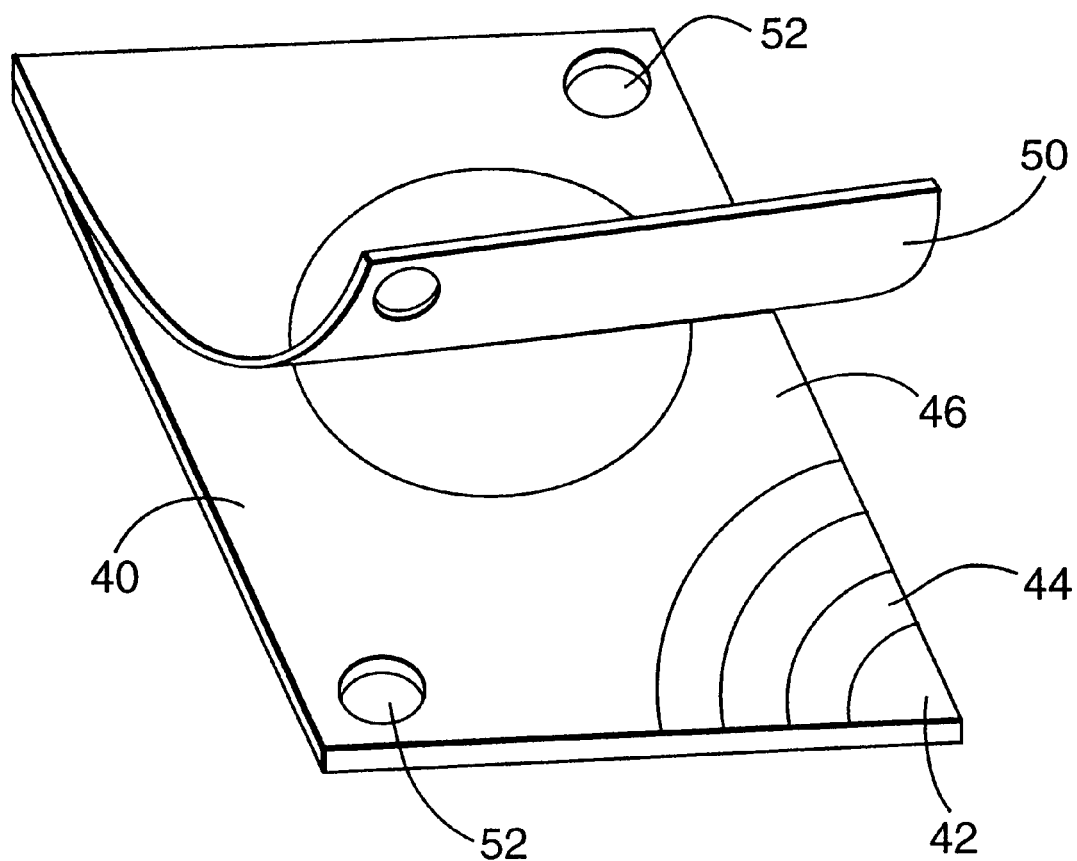
FIG. 2 and FIG. 3 are schematics of a thin film culture device having positioning structures (FIG. 2) and partitioning of a microorganism colony (FIG. 3).

Another suitable culture device that contains multiple layers is shown in FIG. 2. As used herein, the term "layer" includes a solid substrate and any adhesives, indicators, inducers, nutrients, gelling agents, or other reagents coating the solid substrate. The devices may be constructed generally as described above. The device 40 includes a first layer made from a self-supporting solid substrate, such as water impermeable substrate 42. Bottom substrate 42 typically is a relatively stiff material made of a water impermeable material that does not absorb water, such as polyester, polypropylene, polystyrene, or glass. Polyester material is a particularly useful substrate. Other suitable waterproof materials include water permeable substrates such as paper containing a water impermeable polyethylene coating such as "Schoeller Type MIL" photoprint paper (Schoeller, Inc., Pulaski, N.Y.). In general, devices of the invention are constructed using substrates that are transparent or translucent to allow colonies to be viewed. In embodiments where viewing of the colonies is not necessary, opaque substrates may be used. Thickness of the substrate can range from about 0.08 mm to 0.5 mm. For example, polyester films typically are about 0.10 to about 0.18 mm thick, polypropylene films are about 0.10 to about 0.20 mm thick, and polystyrene films are about 0.38 mm thick.

The upper surface of substrate 42 may be coated with growth medium 44, which is then dried to provide a dry medium on substrate 42. Alternatively, adhesive may be coated on substrate 42, which serves to hold a growth medium that may be applied as a powder. The adhesive should be sufficiently transparent when hydrated to allow visualization of microbial colonies growing on the surface of the substrate when viewed through the coated substrate. The adhesive should also be coated on the substrate at a thickness that allows the substrate to be uniformly coated with dry growth medium without completely embedding the medium in the adhesive.

A spacer 46 having a circular opening may be attached to the medium coated surface of substrate 42. Spacer 46 covers the periphery of substrate 42, and defines an area that is to be inoculated with a sample and also serves to prevent the sample from leaking from the substrate. Spacer 46 may be any non-absorbent material such as plastic, including foamed plastic (i.e., a foam) or a non-absorbent non-woven material. The diameter of the circular opening may be altered. For example, a polystyrene foam web may have 5 cm to 6 cm diameter die-cut circular holes and be used with the same volume of sample (approximately 1 ml). It should be noted that for larger surfaces, spacer 46 may have multiple circular openings such that multiple plating surfaces are formed on substrate 42. For example, substrate 42 may be the size of a sheet of paper (e.g., 21.6 cm×27.94 cm), or any other size that is convenient for scanning, and spacer 46 may have multiple openings in it to allow, e.g., multiple platings from the same transformation or platings of different dilutions of the same transformation. In an alternate embodiment, a device may not include a sample-containing spacer. In this device, the amount of sample is contained and sequestered on the substrate by the components of the medium alone.

Top cover sheet 50 is disposed on one edge of an upper surface of spacer 46. Cover sheet 50 is the second layer and is preferably made of a transparent film or sheet material in order to facilitate visualizing, and optionally, counting of microbial colonies present on the substrate. In addition, cover sheet 50 is preferably impermeable to bacteria and water vapor in order to avoid the risk of contamination and deterioration of the components. Materials for cover sheet 50 may be selected to provide the amount of oxygen transmission necessary for the type of microorganism to be grown. For example, polyester films have a low-oxygen permeability and are suitable for growing anaerobic bacteria, while polyethylene films have a high-oxygen permeability and are suitable for growing aerobic bacteria. A preferred material for use as cover sheet 50 is biaxially oriented polypropylene. The cover sheet includes gelling agents, and optionally may include microbial growth medium, inducers, indicators, and/or an adhesive. In addition, the cover sheet can include a reinforcement layer, such as a non-woven material, foam (e.g., polystyrene foam), or film (e.g, a polycarbonate film), for additional support.

It should be noted that the top-bottom orientation of the first and second layers can be reversed from that described above.

The first and second layers of the device may be removably or permanently attached to each other by various methods. For example, hinges, clasps, glue, tape, staples, or clamps may be used to attach the first and second layers to each other. In one embodiment, a pressure-sensitive adhesive is used to attach the first and second layers to each other.

The first and second layers of the culture device each contain positioning structures 52, which allow the culture device to be oriented. Positioning structures 52 may be holes (as pictured in FIG. 2), slits, slots, beveled edges, protrusions or any other raised structure, notches, or any other structure that may be used to orient the culture device. Typically, two or more positioning structures are contained on the thin film culture device. It should be noted, however, that a thin film culture device may contain a single positioning structure if, during the harvesting step, the single positioning structure may be used in combination with the overall configuration of the thin film culture device to be oriented. In addition, combinations of positioning structures may be used, e.g., a hole and a notch. A barcode label may also be on a surface of the culture device to aid sample tracking and identification of the culture device.

Figure 3:
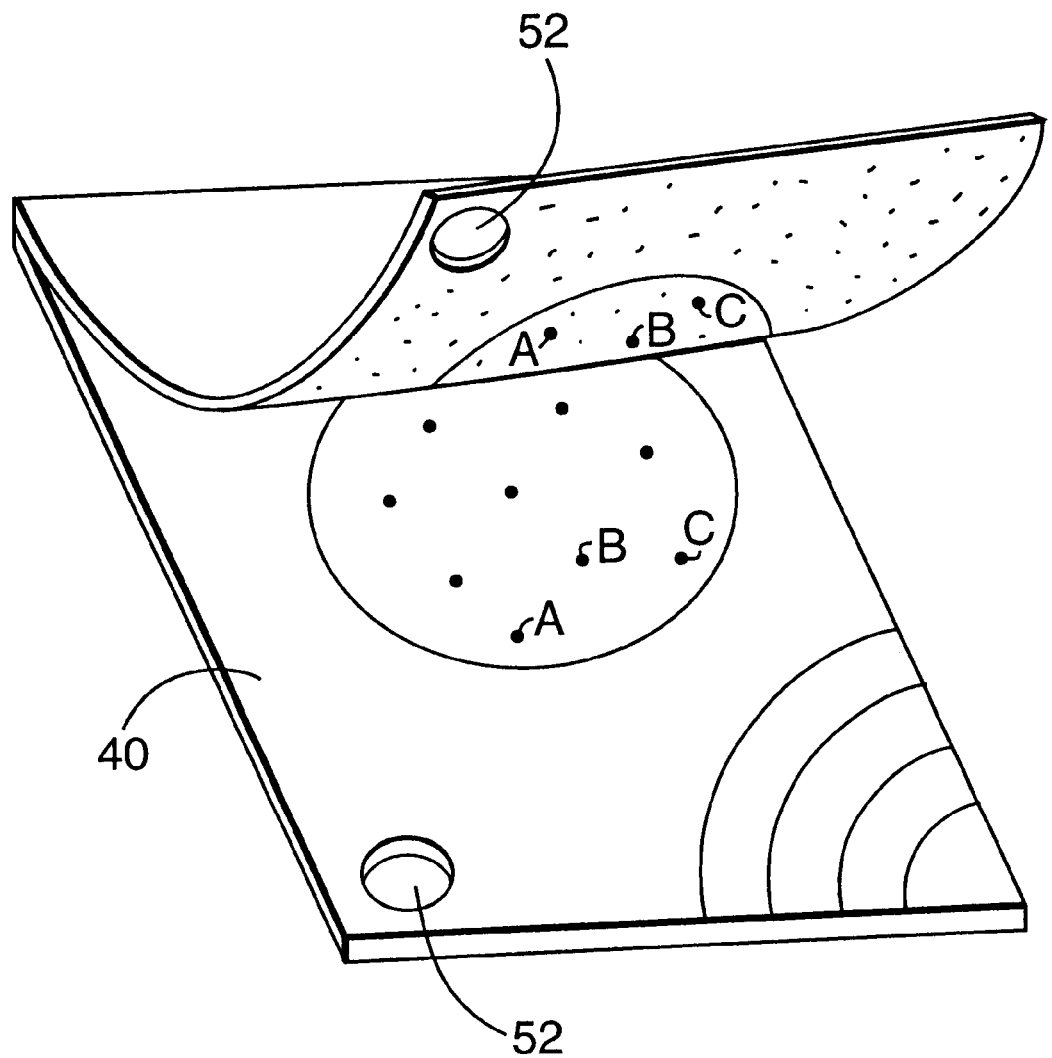

In general, the first and second layers of the device include a gelling agent in an effective amount, i.e., such that, upon separating the layers, portions of most, and preferably, of at least 80% of the visible microorganism colonies are retained on both layers of the device. In other words, at least 80% of the visible microorganism colonies partition to form replicates on the first and second layers after separating the layers. See, FIG. 3 for a diagram of the partitioning of the colony to form replicates. For example, at least 85%, 90%, 95%, or 99% of the colonies can partition and form replicates on the first and second layers. Non-limiting examples of gelling agents include guar, xanthan, locust bean gum, polyvinyl alcohol, carboxymethylcellulose, alginate, polyvinylpyrrolidone, gellan, and polyacrylic acid (low monomer content). Guar is a particularly useful gelling agent. Suitable concentrations for a gelling agent may be determined by using the methods described herein. In general, a device is produced with varying amounts of the gelling agent on the first and second layers. The device is inoculated with an aqueous sample containing microorganisms (e.g., 1 to 5 mls) and incubated for an appropriate length of time (e.g., 16–24 hours). The layers of the device are separated, and the fraction of colonies that are retained on both the first and second layers is determined.

The first layer further may include a growth medium. In some embodiments, the growth medium may be on both the first and second layers. Typically, a gelling agent and growth medium are applied together to the substrate included in the first layer. A suitable growth medium typically contains gelling agent at a concentration of less than 1% weight/volume of solution before dehydration. For example, the gelling agent concentration before dehydration can be 0.4% to 0.9% weight/volume or 0.6% to 0.8% weight/volume. Final amounts of gelling agent in the first layer range from 20 mg to 100 mg/24 in$^2$ after drying. For example, the final amount of gelling agent may be 30 to 80 or 40 to 50 mg/24 in$^2$ in the first layer. The amount of gelling agent in the second layer typically is at least five times (5×) greater or more than five times (e.g., 7×, 8×, 9×, or 10×) than the amount in the first layer. For example, the amount of gelling agent in the second layer may range from 300 to 500 mg/24 in$^2$ or 400 to 450 mg/24 in$^2$. Alternatively, the growth medium may be applied before or during inoculation.

Nutrients in the growth medium may vary depending on the microorganism to be cultured. See, the Handbook of Microbiological Media (2$^{nd}$ Ed., by Atlas, L. C. Parks (ed), 1996, CRC Press, Boca Raton, Fla.) for a description of growth media for culture of bacteria, yeast, and fungi. A growth medium may include a detergent (e.g., an ionic detergent) at a concentration from about 0.5% to about 2% weight/volume of solution before dehydration. Non-limiting examples of detergents include deoxycholate, bile salts and sodium lauryl sulfate.

Additional components of the growth medium can include salts, such as calcium chloride and magnesium chloride, selectable agents, indicators, and inducers. For example, selectable agents may be antibiotics such as such as kanamycin, ampicillin, carbenicillin, spectinomycin, streptomycin, vancomycin, tetracycline, or chloramphenicol. Other selectable agents may be deficiencies in particular amino acids. Indicators may be precipitable, chromogenic, or fluorescent and/or fluorogenic. Suitable fluorescent or fluorogenic indicators include, for example, 4-methylumbelliferyl phosphate (disodium salt trihydrate or free acid), 4-methylumbelliferyl-beta-D-glucopyranoside, 4-methylumbelliferyl-beta-D glucuronic acid, 4-methylumbelliferyl-beta-D-galactopyanoside, fluoroscein diacetate, or fluoroscein antibody conjugates. A precipitable indicator may be, for example, 2,3,5-triphenyltetrazolium chloride. Chromogenic indicators typically are colorless until activation by the microorganism, e.g., enzymatic hydrolysis or reduction of a chemical bond. Non-limiting examples of chromogenic indicators include 5-bromo-4-chloro-3-indoxyl-β-D-glucuronic acid, L-Alanine-5-bromo-4-chloro-3-indoxyl ester (trifluoroacetate salt), 5-bromo-4-chloro-3-indoxyl-1-acetate, 5-bromo-4-chloro-3-indoxyl-3-acetate, 5-bromo-4-chloro-3-indoxyl-N-acetyl-β-D-galactosaminide, 5-bromo-4-chloro-3-indoxyl-N-acetyl-β-D-glucosaminide, 5-bromo-4-chloro-3-indoxyl butyrate, 5-bromo-4-chloro-3-indoxyl caprylate, 5-bromo-4-chloro-3-indoxyl-β-D-cellobioside, 5-bromo-4-chloro-3-indoxyl-α-L-fucopyranoside, 5-bromo-4-chloro-3-indoxyl-β-D-fucopyranoside, 5-bromo-4-chloro-3-indoxyl-β-L-fucopyranoside, 5-bromo-4-chloro-3-indoxyl-α-D-galactopyranoside, 5-bromo-4-chloro-3-indoxyl-β-D-galactopyranoside, 5-bromo-4-chloro-3-indoxyl-α-D-glucopyranoside, 5-bromo-4-chloro-3-indoxyl-β-D-glucopyranoside, 5-bromo-4-chloro-3-indoxyl-β-D-glucuronic acid (cyclohexylammonium salt), 5-bromo-4-chloro-3-indoxyl-β-D-glucuronic acid (sodium salt), 5-bromo-4-chloro-3-indoxyl myo-inositol-1-phosphate (ammonium salt), 5-bromo-4-chloro-3-indoxyl-α-D-maltotriose, 5-bromo-4-chloro-3-indoxyl myristate, 5-bromo-4-chloro-3-indoxyl-α-D-mannopyranoside, 5-bromo-4-chloro-3-indoxyl-nonanoate, 5-bromo-4-chloro-3-indoxyl oleate, 5-bromo-4-chloro-3-indoxyl palmitate, 5-bromo-4-chloro-3-indoxyl phosphate (di{2-amino-2-methyl-1,3-propanediol}salt), 5-bromo-4-chloro-3-indoxyl phosphate (dilithium salt hydrate), 5-bromo-4-chloro-3-indoxyl phosphate (dipotassium salt), 5-bromo-4-chloro-3-indoxyl phosphate (disodium salt sesquihydrate), 5-bromo-4-chloro-3-indoxyl phosphate (potassium salt), 5-bromo-4-chloro-3-indoxyl phosphate (p-toluidine salt), 5-bromo-4-chloro-3-indoxyl sulfate (potassium salt), 5-bromo-4-chloro-3-indoxyl sulfate (p-toluidine salt), 5-bromo-4-chloro-3-indoxyl thymidine-3'-phosphate (cyclohexylammonium salt), or 5-bromo-4-chloro-3-indoxyl-β-D-xylopyranoside. Sodium tellurite also is a suitable indicator.

Inducers stimulate an enzyme to cleave a corresponding indicator. For example, 1-O-methylglucuronic acid is an inducer that stimulates glucoronidase to cleave 5-bromo-4-chloro-3-indoxyl-β-D-glucuronic acid (indicator) to produce a colored product. Other inducer and indicator pairs include 5-bromo-4-chloro-3-indoxyl-β-D-glucuronic acid, sodium salt or 3-indoxyl-β-D-glucuronic acid, sodium salt and isopropyl-β-D-thioglucuronic acid, sodium salt; 5-bromo-4-chloro-3-indoxyl-β-D-galactopyranoside or indoxyl-β-D-galactopyranoside and isopropyl-β-D-thiogalactopyranoside; and 5-bromo-4-chloro-3-indoxyl-β-D-glucopyranoside, 3-indoxyl-β-D-glucopyranoside, or 5-bromo-6-chloro-3-indoxyl-β-D-glucopyranoside and 1-O-Methyl-β-D-glucopyranoside.

A further embodiment of one embodiment of a thin film culture device includes a lac differentiation mechanism. When a thin film culture device includes two chromogenic indicators, the β-galactosidase deficient colonies activate a first indicator and the β-galactosidase producing colonies activate a second indicator, thereby producing two color differentiation. For example, some *Escherichia coli* host-vector systems use a β-galactosidase reporter gene, to denote the presence or absence of foreign DNA inserted into a bacterial plasmid vector. When foreign DNA is not in the vector, the cells express β-galactosidase, which hydrolyzes 5-bromo-4-chloro-3-indoxyl-β-D-galactopyranoside (X-gal) to form an insoluble blue precipitate. When foreign DNA is inserted into the lacZ gene in the plasmid vector, the cells are unable to hydrolyze X-gal. These cells may be readily identified using another reagent, 2,3,5-triphenyltetrazolium chloride (TTC), which turns red in the presence of such cells. In sum, lac$^+$ colonies appear blue and lac$^-$ colonies appear red.

Method and System for Harvesting Cells

Figure 4:
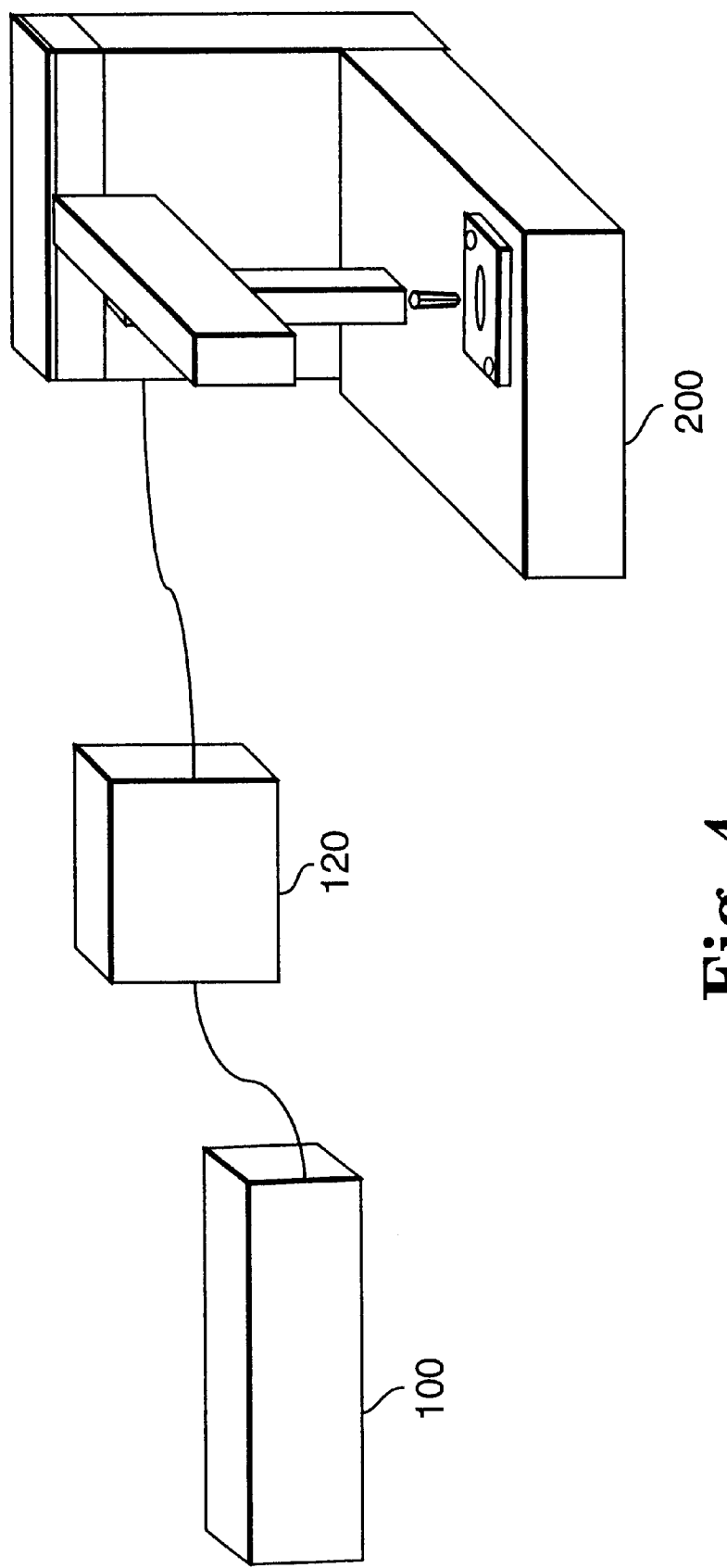
FIG. 4 is a diagram of a system for harvesting cells from a colony on a culture device.

With reference to FIG. 4, culture devices of the invention can be scanned using scanner 100 to obtain an image of the culture device, e.g., a TIFF image, JPEG image, GIFF image, or bitmap. Minimal requirements for a scanner include 500 dots/inch (dpi) for resolving microbial colonies on culture devices of the invention. Commercially available flatbed scanners such as the Astra 2000 (1200 dpi, UMAX Technologies, Inc., Freemont, Calif.) are suitable for scanning and provide adequate resolution. As thin film culture devices typically are transparent from the top and from below, the devices may be scanned from either direction. Furthermore, culture devices of the invention may be scanned at varying magnifications and orientations without loss of fidelity as the positioning structures have a known geometry.

Processing unit 120 stores the scanned image and processes the image using an algorithm that provides location of each of the colonies relative to the positioning structures on the culture device. Processing unit 120 includes a central processing unit (CPU) that forms part of a general purpose computer, such as a PC, Macintosh, or workstation and a display device that includes a viewing screen for graphic output. Processing unit 120 is capable of storing program code, and contains an input device for user input, such as a keyboard or mouse. Processing unit 120 communicates with input devices, a display device, and in some embodiments, a printer, via one or more input/output controllers. Processing unit 120 also is in communication with picking apparatus 200 (see FIG. 6) such that a stored file in processing unit 120 is accessible to picking apparatus 200. In addition, processing unit 120 can be communicatively linked to one or more processing units by a network such that a user can remotely access the raw or processed image. For example, if the raw or processed image is remotely accessible, scanner 100 and processing unit 120 can be in one location, while picking apparatus 200 is at a different location.

Figure 5:
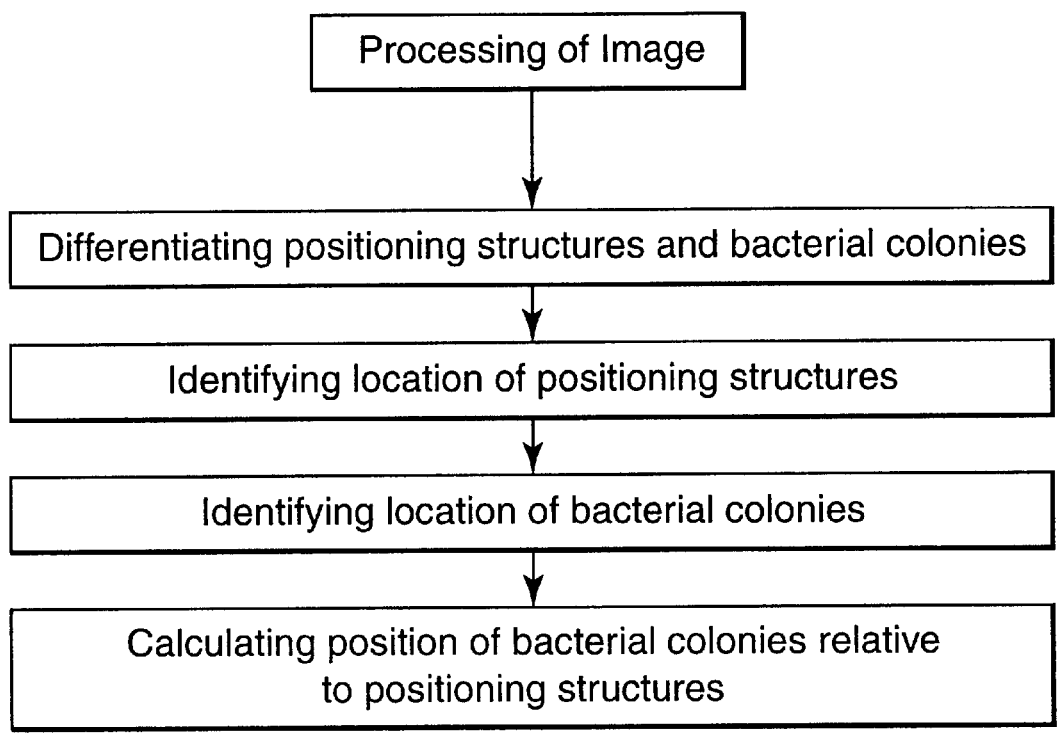
FIG. 5 is a flow diagram of processing steps for calculating the positions of colonies relative to each other and to positioning structures on the culture device.

As indicated in FIG. 5, processing of the image includes differentiating positioning structures and microbial colonies based on a pre-determined threshold, identifying location of positioning structures (by, for example, size discrimination), identifying location of microbial colonies (by, for example, size discrimination), optionally selecting specific microbial colonies and calculating position of microbial colonies relative to the positioning structures (e.g., providing X-Y coordinates of colonies relative to positioning structures).

Component Works IMAQ Vision Software from National Instruments (Austin, Tex.) may be used for the processing. This software package processes the image by first creating a histogram by converting color or black and white images into a gray scale pixel map. Positioning structures and microbial colonies are distinguished by segmenting the pixels into a binary map, based on set levels. Positioning structures and microbial colonies each are identified by grouping pixels into local objects, calculating area of each object, and calculating center of mass coordinates (i.e., X,Y).

Parameters can be set such that colonies of a certain size, e.g., 0.5 to 1.0 mm in diameter, or of a certain color are chosen. Other selection options are also available. One available option uses color differentiation. Using a color imaging system, rather than a black/white imaging system, a RGB (red-green-blue) histogram of each colony may be used to distinguish the color intensity, such as blue vs. red, for each colony on the plate. Another available option uses filter differentiation. Using one or two filters enables a black/white imaging system to distinguish different colored colonies, such as red from blue colonies. For example, with a blue filter, only red colonies would be substantially "visible" to the black/white imaging system. With a red filter, only blue colonies would be "visible". Imaging a culture device with both filters (sequentially) and using a system to maintain registration of the camera with the device also may account for coincidental or overlapping red and blue colonies, thus allowing identification of only pure colonies.

Figure 9:
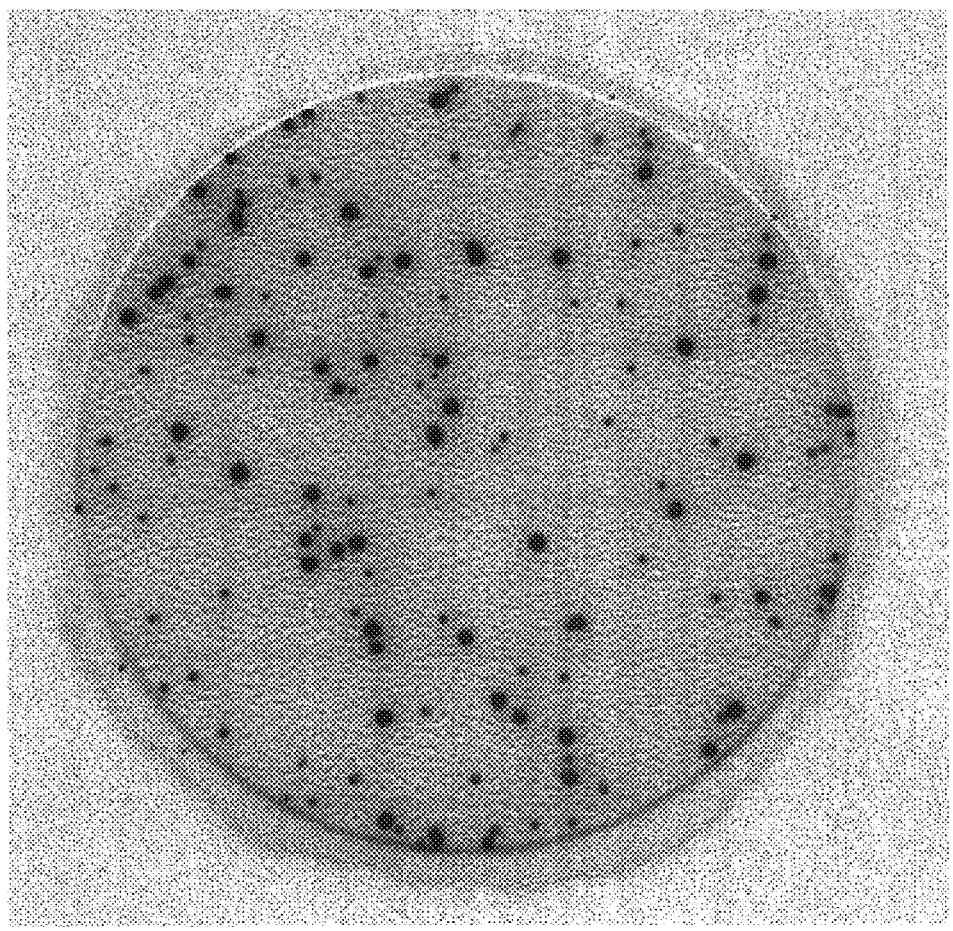
FIG. 9 is a color digital image of a thin film culture device containing lac (+) and lac (−) *E. coli* colonies.

Still another available option uses size differentiation. Appropriate use of control culture devices may facilitate selection of specific colonies on a culture device containing differentiable microorganisms when the selection is based on the size of such colonies. For example, when cells transformed with a plasmid containing a desired DNA insert are to be selected by the size of the colonies, two controls may be used. A first control culture device includes cells transformed with a plasmid that does not have a DNA insert and a second control culture device includes cells transformed with a plasmid that has a DNA insert. Unknown, first control and second control culture devices are all incubated at the same temperature (e.g., 37° C.) for the same length of time and then all three devices are imaged. The average colony size (and standard deviation) of each control culture device strain is determined and a suitable statistical test (e.g., a T-test) is applied to ascertain whether any observed difference in colony sizes between the two control devices are statistically significant. Ideally, the difference in size between "small" and "large" colonies would be greater than the standard deviations of both groups of colony sizes. A threshold value, either an upper or a lower threshold, based on colony sizes of the two control sizes is then used to select desired colonies from the unknown culture device. The unique combination of chromogenic, precipitable indicators in a thin film culture device such as a CLONdisc plates (Clontech Laboratories, Inc., Palo Alto Calif.) affords a technique of distinguishing colony lac phenotypes using colony size. FIG. 9 illustrates a plate containing the indictor system used in the CLONdisc plates. Both lac$^+$ and lac$^-$ derivatives of an *E. coli* strain were inoculated and grown overnight. The figure illustrates the significant differences in the sizes of the red colonies (lac$^-$) and the blue colonies (lac$^+$). In some cases, an indicator combination of one indicator that remains essentially physically associated with the bacteria after changing color (e.g., TTC) and one indicator that results in an accumulation of intracellular and extracellular color formation (e.g., X-gal) results in a measurable differentiation of colony sizes.

Coordinates of the colonies are stored in an appropriate file for the picking apparatus such that cells from colonies on the culture device can be harvested. Custom Visual Basic (VB) software can be used to coordinate processing of the image with the picking apparatus. VB utilizes dynamic linked libraries (DLLs) and ActiveX controls from the IMAQ vision package.

Figure 6:
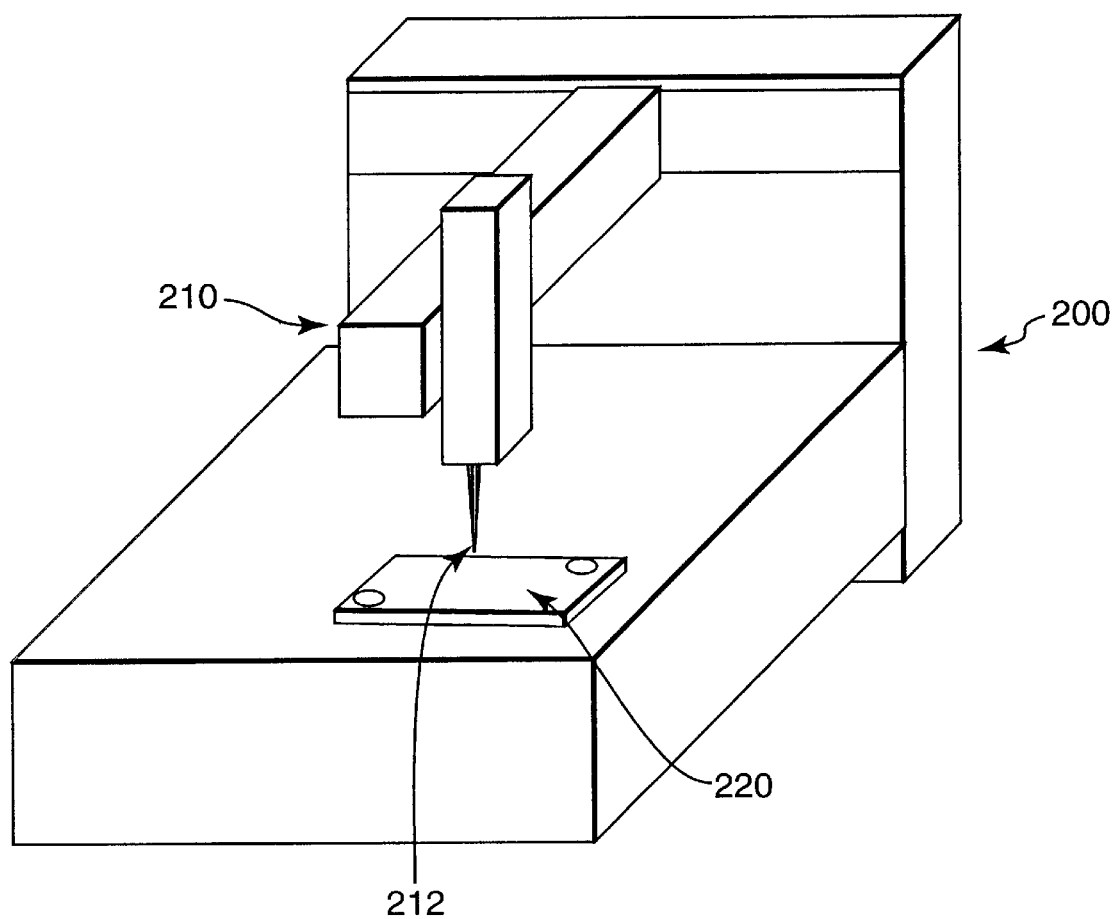
FIG. 6 is a diagram of a picking apparatus.
Figure 7:
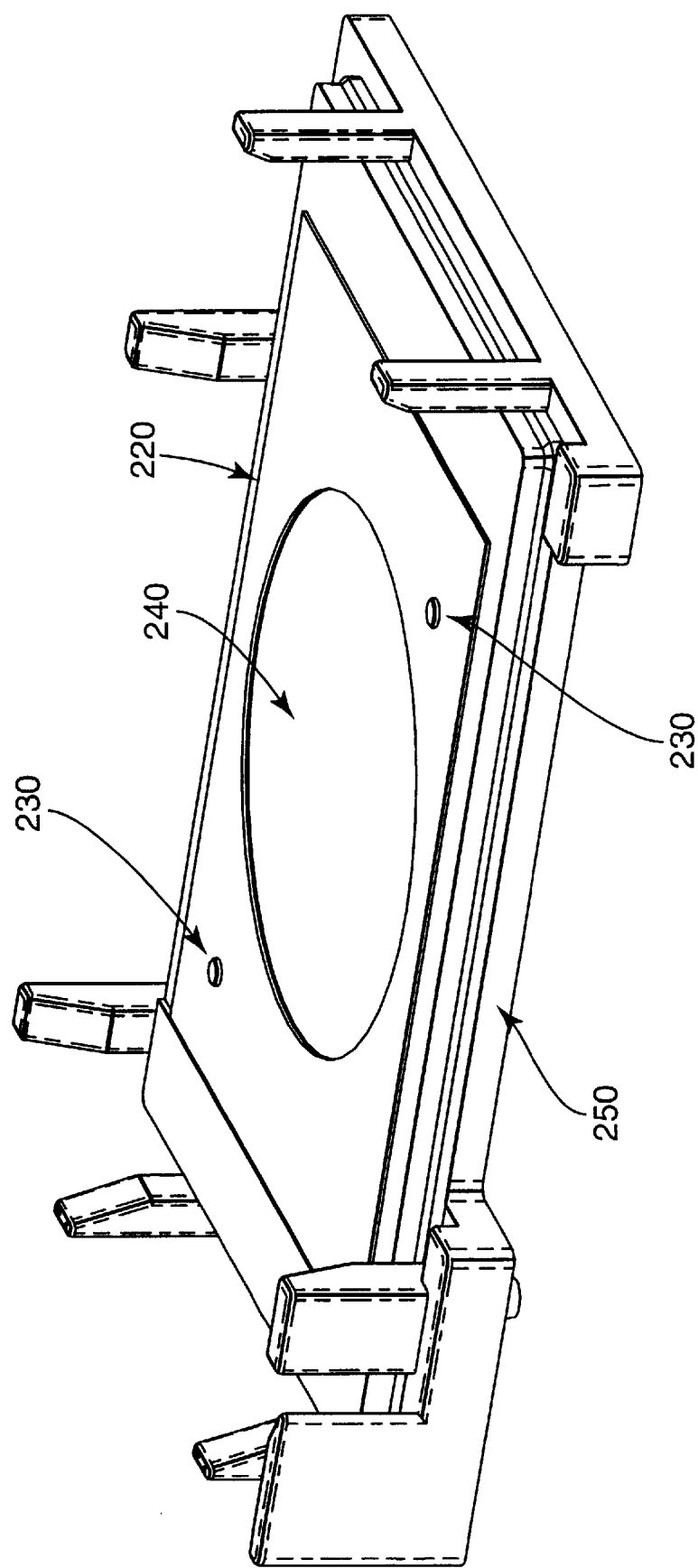
FIG. 7 is a diagram of an orienting unit.
Figure 8:
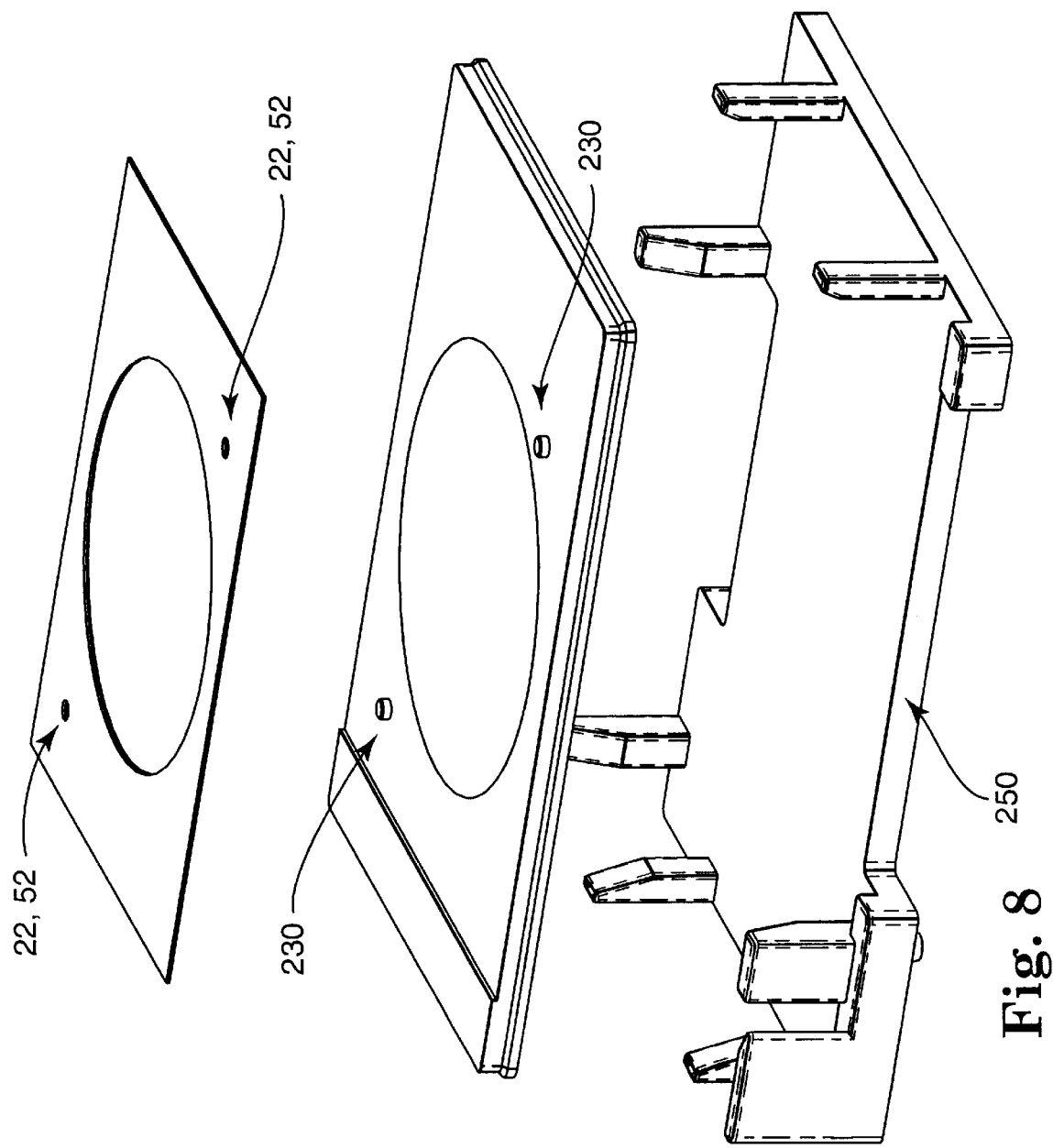
FIG. 8 is a diagram of a culture device being placed on an orienting unit.

The commercially available Biomek 2000 fluidic workstation from Beckman Instruments is an example of a suitable picking apparatus. In the case of the Biomek 2000, coordinates of the colonies are stored in a tool command language (TCL) file. With reference to FIG. 6, picking apparatus 200 contains a processing unit, picking arm 210, liquid handling tip 212, orienting unit 220, and base 250 for receiving the orienting unit (illustrated in FIG. 7). Orienting unit 220 contains receiving structures 230 and, optionally, may include compliant pad 240 (see FIG. 7). Receiving structures 230 receive corresponding positioning structures of the culture device. As illustrated in FIG. 8, if positioning structures 22 or 52 are holes, receiving structures 230 are circular posts. Similarly, if positioning structures 22 or 52 are notches or other structures, receiving structures 230 are complementary to those positioning structures. Compliant pad 240 is composed of a material that can be compressed such that the pipette tip can push into the thin film culture device to harvest cells from colonies without damaging the film. Non-limiting examples of compliant materials that may be used include rubber or foam.

Picking apparatus 200 also is adapted such that it can contact a colony on the culture device to harvest cells by contact and/or aspiration, then transfer the harvested cells to a container, such as a 96-well plate or test tube. For example, picking arm 210 can be configured with liquid handling tip 212, e.g., a pipette tip, plastic tube, or glass tube, for contacting and/or aspirating colonies. Picking arm 210 also can be configured with a solid rod, e.g., a plastic probe or toothpick for contacting colonies. In addition, picking arm 210 can be configured with multiple liquid handling tips and controlled such that a particular tip can be selected (e.g., an active tip could be moved such that it protrudes beyond the other tips). Preferably, liquid handling tip 212 is disposable and is discarded after contact with a colony. For example, the picking apparatus can be programmed such that it retrieves a pipette tip from a container of pipette tips, contacts a colony to harvest cells from that colony, transfers the cells to a defined location on a 96-well plate, and disposes of the pipette tip. Alternatively, the pipette tip can be placed back in the same container from which it was retrieved. In other embodiments, liquid handling tip 212 is cleaned on-line (e.g., washed in circulating water, alcohol, then vacuum dried before use) or cycled through a recycling station where liquid handling tip 212 is cleaned without hindering the picking of colonies.

To increase yield of cells from the colony and to offset any errors in the calculation of the colony coordinates, picking arm 210 can be moved in at least one direction from the contact point, e.g., two or more directions from the contact point. For example, picking arm 210 can moved in a circular or zigzag pattern from the contact point. The uniform surface topography of the culture device allows the picking arm to move over the surface of the colony, whereas for traditional culture devices (e.g., agar plates), the surface topography is more variable, making it less likely that the picking arm contacts a useful amount of colony surface.

Computer Readable Media

The invention also features a programmable processor configured to execute instructions from a computer readable medium, such as a hard-disk, floppy-disk, networked storage device or the like. The computer program is arranged such that when the program is executed, an image of a culture device of the invention is displayed on a display device, positioning structures are differentiated from colonies on the culture device, location of the positioning structures is identified, location of the colonies is identified, and position of the colonies is calculated relative to the positioning structures. In other embodiments, a computer readable medium is featured that has an image stored therein, wherein the image represents the colonies on a culture device of the invention, or that has data stored therein, wherein the data are the coordinates of colonies on a culture device of the invention relative to positioning structures. In addition, the instructions, images, or positioning data may be transmitted within a computer readable medium such as a global computer network for remote processing according to the invention.

The invention will be further described in the following examples, which do not limit the scope of the invention described in the claims.

EXAMPLES

Example 1

Bacterial Cultures

The strains listed in Table 1 were stored on LB agar plates (Miller Formulation, Becton Dickinson Microbiological Systems, Sparks, Md.) containing 50 µg/mL ampicillin (sodium salt, Sigma Chemical Co., St. Louis, Mo.), 40 µM isopropyl-β-D-galactopyranoside (Sigma Chemical Co., St. Louis, Mo.), and 8 mg/L 5-bromo-4-chloro-3-indoxyl-β-D-galactopyranoside (Biosynth AG, Staad, Switzerland). *E. coli* DH5α was obtained from Clontech Laboratories, Inc. (Palo Alto, Calif.). *E. coli* XL1-Blue was obtained from Stratagene, Inc., La Jolla, Calif. Plasmid pHB2 is a derivative of pUC19 in which DNA has been inserted into the Multiple Cloning Site of the lac-complementing region. Plasmid pGFPuv was obtained from Clontech Laboratories and had a very low level of residual β-galactosidase activity, thus making the colonies appear lac$^-$ on CLONdisc plates and on agar plates containing X-gal. Colonies from each strain were inoculated into 17×100 mm sterile snap-cap plastic tubes containing 5-mL of LB broth containing 50 µg/mL ampicillin. The tubes were capped, placed into a 37° C. environmental shaker, and agitated at 220 rpm.

TABLE 1

| 3M Strain Number | *E. coli* Strain | Plasmid | Lac Phenotype |
| --- | --- | --- | --- |
| GPM-1 | DH5α | pUC19 | Positive |
| GPM-51 | DH5α | pHB2 | Negative |
| GPM-350 | XL1-Blue | pUC19 | Positive |
| GPM-351 | XL1-Blue | pGFPuv | Negative |

Plate Inoculation

Two sterile diluents were prepared: I) 0.85% NaCl (Hardy Diagnostics, Santa Maria, Calif.) containing 50 µug/mL ampicillin and 40 µM isopropyl-β-D-galactopyranoside and II) LB Broth containing 50 µg/mL ampicillin and 40 µM isopropyl-β-D-galactopyranoside. After 7 hours of incubation, the cultures were diluted serially (10-fold steps) into each of the diluents listed above. A 5-mL diluting pipettor (3M Microbiology Products, St. Paul, Minn.) was used to prepare the inocula as follows: 1) 2.9 mL of the diluent was withdrawn into a sterile pipette tip, 2) 0.1 mL of the diluted cell suspension was withdrawn into the same pipette tip, and 3) the entire 3.0 mL mixture was used to inoculate CLONdisc plates (lot # 2002 08 PB, Clontech Laboratories, Palo Alto, Calif.) according to the manufacturer's instructions. After inoculation, the plates were incubated in stacks up to 8 per stack at 37° C. for 24 hours.

Plate Imaging and Analysis

The incubated plates were scanned using a ScanJet 6100C flat-bed scanner (Hewlett-Packard, Palo Alto, Calif.). The scanned images were analyzed using Adobe Photoshop software version 5.0 (Adobe Systems, Inc., San Jose, Calif.). Ten colonies were randomly chosen from the images of four different plates containing bacterial strains GPM-1, GMP-51, GPM-350, or GPM-351. The images were zoomed to 1600× and the number of pixels with the darkest color intensity were counted for each colony. Table 2 shows the number of pixels for each colony type and the average colony size (in pixels).

TABLE 2

Number of pixels comprising the darkest-colored areas of random colonies chosen from the plates inoculated with bacterial strains GPM-1, GPM-51, GPM-350 or GPM-351

|  | GPM-1 | GPM-51 | GPM-350 | GPM-351 |
| --- | --- | --- | --- | --- |
| Colony 1 | 42 | 9 | 81 | 9 |
| Colony 2 | 42 | 9 | 81 | 16 |
| Colony 3 | 56 | 6 | 64 | 12 |
| Colony 4 | 36 | 25 | 100 | 9 |
| Colony 5 | 49 | 16 | 64 | 16 |
| Colony 6 | 36 | 6 | 81 | 9 |
| Colony 7 | 42 | 9 | 81 | 12 |
| Colony 8 | 42 | 16 | 100 | 16 |
| Colony 9 | 42 | 16 | 56 | 16 |
| Colony 10 | 49 | 25 | 81 | 16 |
| Average | 43.6 +/− 6.1 | 13.7 +/− 7.1 | 78.9 +/− 14.5 | 13.1 +/− 3.2 |

On average, the size (area) of the blue lac$^+$ colonies was larger than the size of the corresponding red lac$^-$ colonies of the same host *E. coli* strain. Furthermore, the lac$^+$ colonies were larger than then corresponding lac$^-$ colonies whether the diluent consisted of saline or a nutrient solution, such as LB broth.

Example 2

*E. coli* strain DH5α cells were made competent using CaCl$_2$ then transformed with pUC19 or pUC19 derivatives containing inserts of various sizes. After transformation and recovery, all cells were mixed and diluted in Butterfield's buffer containing ampicillin (50 µg/ml) and 1 ml of the diluent was plated on a thin film culture device capable of differentiating recombinants and non-recombinants. The culture device was constructed as described in Example 1 of U.S. patent application Ser. No. 09/541,416, filed Apr. 3, 2000, except that the culture device had two 0.32 cm positioning holes in opposite corners and a reinforcing foam sheet was adhered to the cover sheet. Plates were incubated at 37° C. for 14 to 18 hours then scanned.

The culture device was placed face down on a Umax 2000 flatbed scanner (Model: Astra 1200P, 1200 dpi, Freemont, Calif.) and a bitmap file of the culture device was obtained. The bitmap file was processed such that colonies were identified by color, intensity level, and minimum/maximum size. Colonies were mapped into picture units with respect to the positioning structures. The colony map was resized and rotated into coordinates using the known geometric location of the positioning structures. As the culture device was designed to be peeled open before picking colonies, the mirror image was generated for the robotic workstation to produce transformed colony coordinates. Transformed colony coordinates were downloaded into an appropriate instruction file for a Biomek robot (TCL file). Beckman Biomek software was initiated from the program processing the image, and the Biomek software executed the revised colony picking algorithm based on the colony coordinates.

The culture device was positioned on the orienting unit of the workstation that contained receiving structures adapted to receive the corresponding positioning structures on the culture device. The robotic arm used a P20 pipetting tool and selected pipette tips from a pipette holder. A 1 mm zigzag motion was used to increase the yield of bacteria picked from the colony and to compensate for any mapping error. Picked bacteria were transferred into incubation broth at a unique location in a 96-well plate. The pipette tip was returned back to its original location in the pipette holder, and a new pipette tip was selected for the next pick.

Each well of the 96-well plate contained 1.2 ml of LB and 50 µg/ml ampicillin. Cultures were grown at 37° C. for 16 hours with shaking (200 rpm). Growth was observed in 85 of the wells (88.5%) and plasmid DNA was isolated from the cultures using the alkaline lysis method. Plasmids were cut with EcoRI and electrophoresed through an 0.7% agarose gel. Ethidium bromide staining of the gel indicated that different colonies were picked and plasmids of varying sizes were isolated.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A culture device for the propagation or storage of microorganisms, said device comprising a self-supporting, waterproof substrate and a cover sheet, wherein a gelling agent is contained on said self-supporting substrate, and wherein said self-supporting substrate and said cover sheet comprise positioning structures constructed so as to cooperate with a receiving structure.

2. The culture device of claim 1, wherein said positioning structures are holes, slits, slots, beveled edges, notches, or raised structures.

3. The culture device of claim 1, said culture device further comprising a barcode label on a surface of said culture device.

4. The culture device of claim 1, wherein said cover sheet is transparent.

5. The culture device of claim 1, wherein said self-supporting substrate further comprises a spacer.

6. The culture device of claim 1, wherein said self-supporting substrate further comprises a culture medium.

7. The culture device of claim 1, wherein said cover sheet further comprises a gelling agent.

8. The culture device of claim 1, wherein said cover sheet further comprises a reinforcement layer.

9. The culture device of claim 8, wherein said reinforcement layer is selected from the group consisting of a foam, a film, or a non-woven material.

10. The culture device of claim 1, wherein said device further comprises an indicator and a corresponding inducer.

11. The culture device of claim 1, wherein said device further comprises two chromogenic indicators providing different colors for differentiating microorganisms.

12. A culture device for the propagation or storage of microorganisms comprising first and second layers, said first and second layers comprising a gelling agent, said first and second layers further comprising positioning structures constructed so as to cooperate with a receiving structure, and wherein said first and second layers are separable from each other.

* * * * *

UNITED STATES PATENT AND TRADEMARK OFFICE
CERTIFICATE OF CORRECTION

PATENT NO. : 6,756,225 B2
DATED : June 29, 2004
INVENTOR(S) : Bedingham, William It is certified that error appears in the above-identified patent and that said Letters Patent is hereby corrected as shown below:

Column 7,
Line 67, after "beta-D-" replace "galactopyanoside" with -- galactopyranoside --;

Column 12,
Line 49, after "50" delete "$\mu$ug/mL" and insert in place thereof -- $\mu$g/mL --;

Signed and Sealed this

Seventh Day of June, 2005

JON W. DUDAS
*Director of the United States Patent and Trademark Office*